(12) United States Patent
Sugiura

(10) Patent No.: US 8,157,721 B2
(45) Date of Patent: Apr. 17, 2012

(54) ARTIFICIAL HEART PUMP SYSTEM AND ITS CONTROL APPARATUS

(75) Inventor: Naoya Sugiura, Kanagawa (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 176 days.

(21) Appl. No.: 12/347,775

(22) Filed: Dec. 31, 2008

(65) Prior Publication Data

US 2009/0118827 A1 May 7, 2009

Related U.S. Application Data

(62) Division of application No. 10/864,431, filed on Jun. 10, 2004, now Pat. No. 7,563,225.

(30) Foreign Application Priority Data

Jun. 12, 2003 (JP) ................................. 2003-168137
Jun. 12, 2003 (JP) ................................. 2003-168138
Jun. 12, 2003 (JP) ................................. 2003-168139

(51) Int. Cl.
*A61M 1/12* (2006.01)

(52) U.S. Cl. ............ 600/16; 600/17; 623/3.1; 623/3.11; 623/3.13; 623/3.14; 623/3.15; 623/3.16; 623/3.17; 623/3.26; 623/3.27; 623/3.28

(58) Field of Classification Search .................... 623/3.1, 623/3.11, 3.13–3.17, 3.26–3.28; 600/16–17
See application file for complete search history.

(56) References Cited

U.S. PATENT DOCUMENTS

| | | | |
|---|---|---|---|
| 4,928,690 A | 5/1990 | Heilman et al. | |
| 5,078,134 A | 1/1992 | Heilman et al. | |
| 5,383,840 A | 1/1995 | Heilman et al. | |
| 6,123,726 A | 9/2000 | Mori et al. | |
| 6,129,660 A | 10/2000 | Nakazeki et al. | |
| 6,137,416 A | 10/2000 | Meador | |
| 6,142,752 A | 11/2000 | Akamatsu et al. | |
| 6,183,412 B1 | 2/2001 | Benkowski et al. | |
| 6,547,530 B2 | 4/2003 | Ozaki et al. | |

FOREIGN PATENT DOCUMENTS

JP 5-208047 A 8/1993

(Continued)

OTHER PUBLICATIONS

European Patent Office Search Report dated Sep. 2, 2004.

(Continued)

*Primary Examiner* — Carl H Layno
*Assistant Examiner* — Deborah Malamud
(74) *Attorney, Agent, or Firm* — Buchanan Ingersoll & Rooney PC

(57) ABSTRACT

An artificial heart pump system is provided independently with a controlling processor for controlling an operation status of a blood pump so as to perform in a preset condition and with an observing processor for controlling a display unit displaying an operation status and an operation condition of the blood pump. In addition, a memory device is mounted in an outside-the-body type battery pack included in the artificial heart pump system; data such as pump data, event log or the like is stored therein; and data are collected and managed automatically by a battery charger when charging the battery charger for a daily performance. Further, an interface unit of an artificial heart pump is proposed where a user can confirm displayed contents of the controller without exposing the controller externally.

15 Claims, 11 Drawing Sheets

FOREIGN PATENT DOCUMENTS

| | | |
|---|---|---|
| JP | 05-208047 A | 8/1993 |
| JP | 9-056812 A | 3/1997 |
| JP | 09-122228 A | 5/1997 |
| JP | 9-122228 A | 5/1997 |
| JP | 10-085322 A | 4/1998 |
| JP | 11-076394 A | 3/1999 |
| JP | 2000-051372 A | 2/2000 |
| JP | 2000-107281 A | 4/2000 |
| JP | 2000-341428 A | 12/2000 |
| JP | 2001-078068 A | 3/2001 |
| JP | 2001-327595 A | 11/2001 |
| JP | 2002-262357 A | 9/2002 |
| WO | WO 98/14225 | 4/1998 |
| WO | WO 99/17819 | 4/1999 |
| WO | WO 02/098271 A2 | 12/2002 |

OTHER PUBLICATIONS

European Patent Office Communication dated May 18, 2007.
European Patent Office Communication dated Jun. 6, 2008.
Japanese Patent Office Official Action dated Oct. 12, 2007.
(2) Japanese Patent Office Official Actions dated Oct. 15, 2007.

ARTIFICIAL HEART PUMP SYSTEM AND ITS CONTROL APPARATUS

This application is a divisional application of U.S. application Ser. No. 10/864,431 filed on Jun. 10, 2004, the entire content of which is hereby incorporated by references.

BACKGROUND OF THE INVENTION

1. Field of the Invention

The present invention relates to an artificial heart pump system and a controller utilized for its control and more particularly to an artificial heart pump system where a plurality of processors are provided in the control apparatus and a load burdened in one processor is reduced.

2. Description of the Related Art

In a conventional assisted artificial heart pump system, it was proposed a system where a sensor circuit for discriminating a floating position of an impeller is built-in in a pump body in order to establish compatibility between a blood pump body and a controller which are used for an artificial heart (see Jap. laid-open Pat. No. 2001-327595).

Also, as a control method of a blood pump used such as for an artificial heart and for an artificial heart and lung where of the blood pump is assisting or completely displacing a living-body heart by being bypass connected, there was known a method in which the current flowing in the blood pump is controlled to be constant so as to restrain a flowing rate change of the blood pump in a small range with respect to a variation of a pressure load (see Jap. laid-open Pat. No. 9-56812).

Further, there was known a centrifugal type blood pump apparatus which is an control apparatus of a blood pump used for an artificial heart and lung apparatus where a relation between a current flowing through a motor of a blood pump apparatus and a motor rotational frequency and discharging flow rate is memorized beforehand such that a current amount control of a motor, a floating position control of an impeller, a rotation torque control of the impeller, calculation of a liquid viscosity and the like are performed according to an instruction from a processor (CPU) in the controller (see Jap. laid-open Pat. No. 11-76394).

However, the controllers used for the artificial heart pump system which were described in these conventional technologies did not have a processor, were all formed by analog circuits, only a monitor was controlled by a processor even if a processor was included and the control of a motor or a bearing thereof was performed by analog circuits. Also, with respect to the controller used for these pump control apparatuses, all controls for a liquid pump and a display means were performed only by one CPU (processor).

FIG. 1 shows an example of a conventional and portable type artificial heart pump system. In this artificial heart pump system, a centrifugal type rotary blood pump 50 which has an impeller inside is implanted inside a human body. Then, a controller 51 and two batteries 52 and 53 for supplying electric power thereto are held externally in a portable manner. A display unit 54 for user interface is provided in the controller 51.

The blood pump 50 is implanted inside the human body and connected to the portable controller 51 through a cable 55 which passes through a skin.

FIG. 2 is a block constitutional diagram showing an inside constitution of a controller normally used in a conventional artificial heart pump system. The artificial heart pump system is composed of a blood pump 100 (corresponding to the blood pump 50 in FIG. 1) which is implanted inside a human body, a controller 101 (corresponding to the controller 51 in FIG. 1) for controlling an operation status of the blood pump 100, and a battery 102 (corresponding to batteries 52 and 53 in FIG. 1) for supplying electric power to a power supply circuit of the controller 101.

Then, controller 101 is provided with a processor 103 which supervises a control of the whole controller; a memory device 104 which saves observation data of an operation status of the blood pump 100; an operation condition of the blood pump or the like; a magnetic floating control circuit 105 for magnetically float-controlling the impeller which consist of the blood pump 100; a motor driving circuit 106 for drive-controlling the motor which rotates the impeller; a processor 103; a memory device 104; a magnetic floating control circuit 105; a power supply circuit 107 for supplying electric power to the motor driving circuit 106; a liquid crystal display unit (LCD) 108 for displaying a rotational frequency of the impeller of the blood pump, a blood flow rate, a discharging pressure or the like; an LED light emitting device 109 for displaying whether the operation of the blood pump and aforesaid controller is normal or abnormal; a buzzer 110 for announcing an abnormality of the blood pump and aforesaid controller; and an instruction button 111 for instructing, with respect to the processor 103, a change of the pump activation, a change of the LCD displaying content, a release of an abnormal status or the like.

Hereinafter, the operation of the conventional artificial heart pump system shown in FIG. 2 will be explained. An impeller provided inside the blood pump 100 is controlled by the magnetic floating control circuit 105 so as to be floating magnetically and at the same time controlled by the motor driving circuit 106 so as to rotate in a stable rotational frequency. The rotational frequency of the motor for rotating the impeller will be set by a medical staff taking a blood viscosity, a discharging flow rate or the like of a patient into consideration and is normally set to be in a range of 1300 rpm to 2200 rpm.

The processor 103 receives signals from the magnetic floating control circuit 105 and motor driving circuit 106 and make the memory device 104 store necessary information and at the same time makes the liquid crystal display device (LCD) 108 display the operation status of the blood pump 100. The displayed contents of the LED 108 are a rotational frequency of the impeller, a blood flow rate, a discharging pressure of the blood pump and the like.

In a case when an abnormality of the blood pump 100 is detected, the processor 103 makes the displayed color of the LED light emitting device 109 change from green to red and at the same time makes the buzzer 110 activated so as to generate warning sounds.

Also, in the memory device 104, not only the operation status of the blood pump 100 is recorded but also a condition setting for activating the blood pump is stored beforehand such that the processor 103 reads in the setting value stored in the memory device 104 and is to control the operation status of the blood pump 100.

However, in the conventional artificial heart pump system shown in FIG. 2, the processor 103 possessed by the controller 101 is only one. Consequently, all of the processes in the controller 101 should be performed by the processor 103.

More specifically, the processor 103 should perform all of the processes such as the magnetic floating control of the pump 100, the motor rotational frequency control, the data saving process, the data displaying process and the alarm rumbling process.

This means that a very heavy load is requested with respect to the processor 103 and a processor of a high performance having a performance which can execute all of them should be installed. In other words, a high cost is requested for the processor.

Also, in a case when all the processes are performed by one processor 103 in this manner, the software operated on the processor 103 becomes complicated and consequently, productivity and maintainability will be lowered such that a large amount of cost is to be necessary for keeping them.

Further, in a case when the processor 103 stops caused by some kind or another trouble, the controller 101 cannot continue the above mentioned all processes. In this stage, the controller 101 stops its function and there might happen that even a warning notice cannot be emanated.

In an artificial heart pump system, the most important thing is to continue the pump operation safely and it was necessary to provide a processor of a high performance for securing security in aforesaid conventional artificial heart pump system which uses a single processor.

FIG. 3 shows an assisted artificial heart apparatus described in the specification of U.S. Pat. No. 6,183,412. In this assisted artificial heart apparatus, a rotational pump 50 and a flow rate gauge 51 are implanted inside a human body. Then, units provided outside of the body of a patient are a portable type controller 52, a clinical data collecting device 53 for collecting clinical data and a home support system 54 of the patient.

[Cited Patent References]
(1) Jap. Laid-open Pat. No. 2001-327595
(2) Jap. Laid-open Pat. No. 09-056812
(3) Jap. Laid-open Pat. No. 11-076394
(4) U.S. Pat. No. 6,183,412

SUMMARY OF THE INVENTION

An artificial heart pump system according to the present invention was invented to solve the above mentioned various problems and has an object to propose a controller of a pump system for an artificial heart where two processors for a control system and for a display system are provided and it becomes needless to provide a complicated software and at the same time needless to make the performance of the hardware advanced in particular by reducing the processes performed in the respect processors.

In order to achieve the aforesaid object of the present invention, the artificial heart pump system according to the present invention comprises a blood pump implanted inside a body; and a control apparatus (controller) arranged outside of the body in a portable manner for controlling said blood pump, wherein the control apparatus is provided independently with a controlling processor for controlling the operation status of the blood pump so as to be performed under a preset condition and with an observing processor for controlling the operation status of the blood pump and a display unit for displaying the operation condition.

Also, as a preferred exemplified embodiment according to the present invention, it is characterized in that the controlling processor and the observing processor provided in the control apparatus are connected to each other and if one of the processors is in a stop status, the other one of the processors transmits a reset signal to the one of the processors so as to make the latter return to an operation status.

Further, as a preferred exemplified embodiment according to the present invention, it is characterized in that a memory device for memorizing the operation status of the blood pump is provided and this memory is controlled by the observing processor.

In addition, as a preferred exemplified embodiment according to the present invention, it is characterized in that the control apparatus is provided with a setting change instructing unit for changing a setting of the operation condition of the blood pump; the observing processor receives an instruction from the setting change instructing unit and transmit it to the controlling processor such that the controlling processor carries out a setting change of the operation condition of the blood pump.

Furthermore, the control apparatus (controller) used in the artificial heart pump system according to the present invention comprises a magnetic floating control circuit for controlling a floating position of an impeller of an impeller built-in type blood pump; a motor driving circuit for controlling a rotational frequency of the impeller; a controlling processor for controlling the magnetic floating control circuit and the motor driving circuit; a liquid crystal display unit for displaying an operation condition and an operation status of the blood pump; an abnormality display unit for displaying an abnormality of the operation status of the blood pump; a memory device for memorizing an operation condition and an operation status of the blood pump; and an observing processor for controlling these of the liquid crystal display unit, the abnormality display unit and the memory device, wherein the controlling processor and the observing processor are connected to each other for a cooperative operation.

According to an artificial heart pump system and a control apparatus (controller) used therein, a plurality of processors which function as a central unit of the control apparatus are provided separately by dividing for a control system and for a display system and processes which one processor performs are made reduced such that the complexity of the software in each processor can be lowered. Then, it becomes possible to keep the processors equipped in a control apparatus in a low cost.

Further, a plurality of processors are built-in such that the whole system does not stop and it becomes effective for safety measures even if one processor becomes in an activation-stop status, because the other processor can be continued in its operation independently.

DESCRIPTION OF THE PREFERRED EMBODIMENTS

Figure 4:
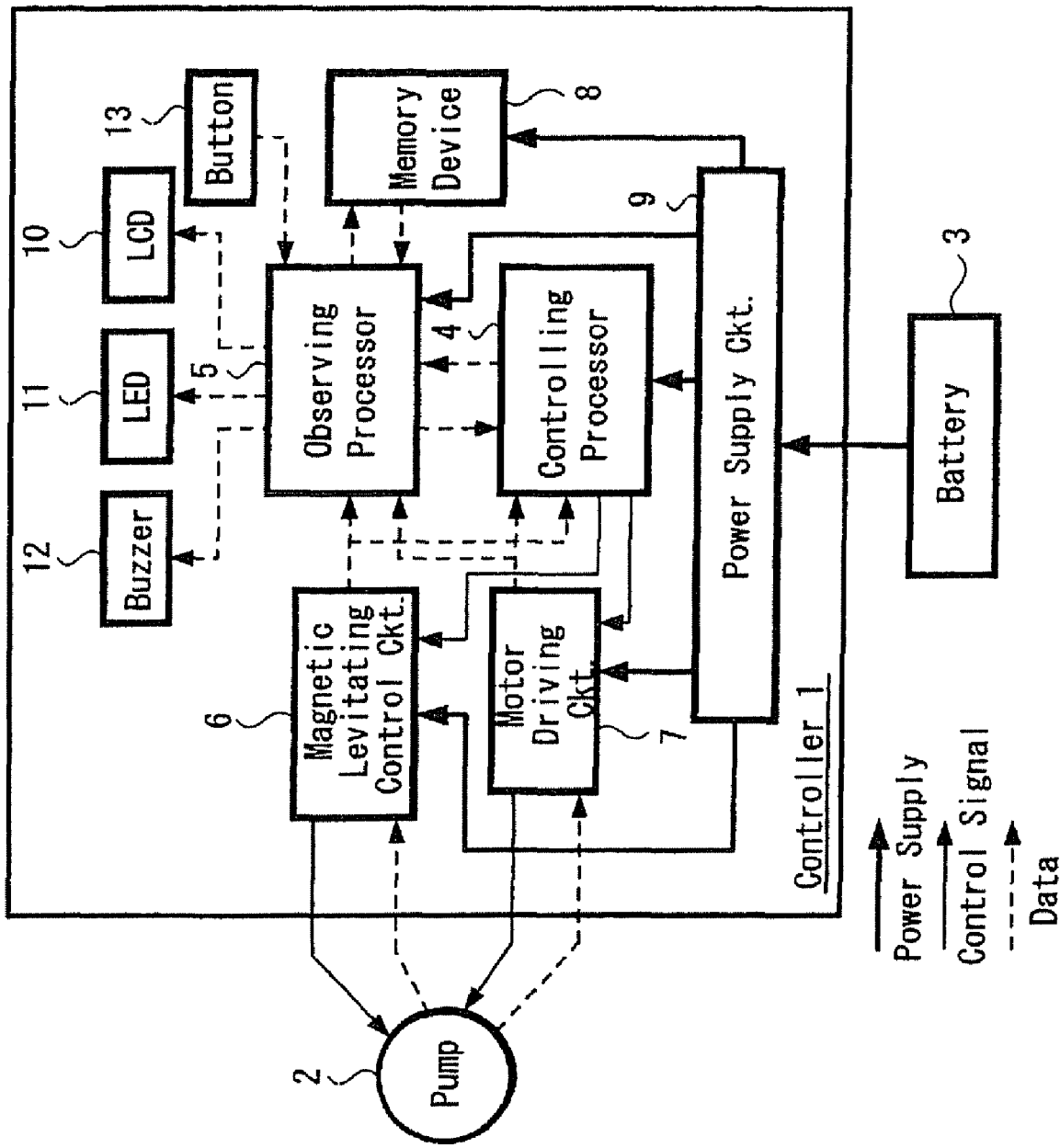
FIG. 4 is a constitutional block diagram showing an exemplified embodiment of an artificial heart pump system using a multi-processor according to the present invention.

FIG. 4 is a block constitutional diagram showing an exemplified embodiment of an artificial heart pump system using a multi-processor according to the present invention. This artificial heart pump system is constituted by a controller 1, a blood pump 2 and a battery 3.

As shown in FIG. 4, the controller 1 is provided with two processors of a controlling processor 4 which supervises the control of a blood pump 2 and a control system in the controller 1 and of an observing processor 5 which supervises the control of a display system. Then, controller 1 is composed, other than aforesaid controlling processor 4 and observing processor 5, of a magnetic floating control circuit 6 for floating an impeller in the blood pump 2 magnetically and controlling its floating position; a motor driving circuit 7 for driving a motor which rotates the impeller; a memory device 8 for receiving and accumulating data showing an operation status of the blood pump 2 from the observing processor 5; these controlling and observing processor 4 and 5; a magnetic floating control circuit 6; a power supply circuit 9 for supplying electric power to the motor driving circuit 7 and memory circuit 8; a liquid crystal display unit (LCD) 10 for displaying a rotational frequency of the impeller of the blood pump 2, a blood flow rate, a discharging pressure or the like; a light emitting device (LED) 11 as an abnormality display means for displaying whether or not the operation of the blood pump 2 and the controller 1 is normal; a buzzer 12 as an abnormality informing means for announcing an abnormality of the blood pump 2 and the controller 1; and an instruction button 13 for instructing, with respect to the observing processor 5, a change of the activation of the pump 2, a change of the LCD displaying content, a release of an abnormal status or the like.

In FIG. 4, thin solid lines designate control signals, dotted lines designate flows of data signals, and bold solid lines designate electric power supplies.

Hereinafter, the operation of an example of an exemplified embodiment according to the present invention shown in FIG. 4 will be explained. According to this example, the controlling processor 4 and the observing processor 5 cooperate with each other and operate so as to reduce loads on each other. More specifically, as shown by arrow marks of thin solid lines, the controlling processor 4 controls the magnetic floating control circuit 6 and the motor driving circuit 7 so as to control a magnetic floating position of the impeller in the blood pump 2 and at the same time to control the rotation of the motor which drives the impeller.

On the other hand, floating position data of the impeller in the blood pump 2 are detected by a detector which is not shown and are supplied to the controlling processor 4 and the observing processor 5 through the magnetic floating control circuit 6. In addition, data signals of the detected rotational frequency of the motor are also supplied to the controlling processor 4 and the observing processor 5 through the motor driving circuit 7.

The controlling processor 4 receives the detected signal of the operation status as mentioned above from the blood pump 2 and controls the magnetic floating control circuit 6 and the motor driving circuit 7. Then, the observing processor 5 always stores the data signal designating the operation status of aforesaid blood pump 2 into the memory device 8 and makes the liquid crystal display device (LCD) 10 display it. It is possible to set properly the contents which are displayed on the LED 10 according to a patient who is a user thereof and it can be contemplated to display a set discharging flow rate and an executed discharging flow rate, set discharging pressure and executed discharging pressure, temperature of the blood, blood viscosity, a rotational frequency of the impeller or the like.

Also, in a case when abnormality occurs in the blood pump 2, the observing processor 5 changes the displayed color of the LED 11 as an abnormality display means, for example, from green to red color and activates the buzzer 12 as an abnormality informing means so as to emanate warning sounds in order to announce the abnormality to a user. Further, in a case when a user or a medical staff changes a setting of an operation condition or the like of the blood pump 2, a control signal of a changing instruction is transmitted to the observing processor 5 by operating the instruction button 13 for a changing instruction.

Then, this control signal is transmitted from the observing processor 5 to the memory device 8 so as to rewrite the set value stored in the memory device 8 and at the same time it is transmitted to the controlling processor 4 so as to change the operation condition of the magnetic floating control circuit 6 and the motor driving circuit 7.

Figure 5:
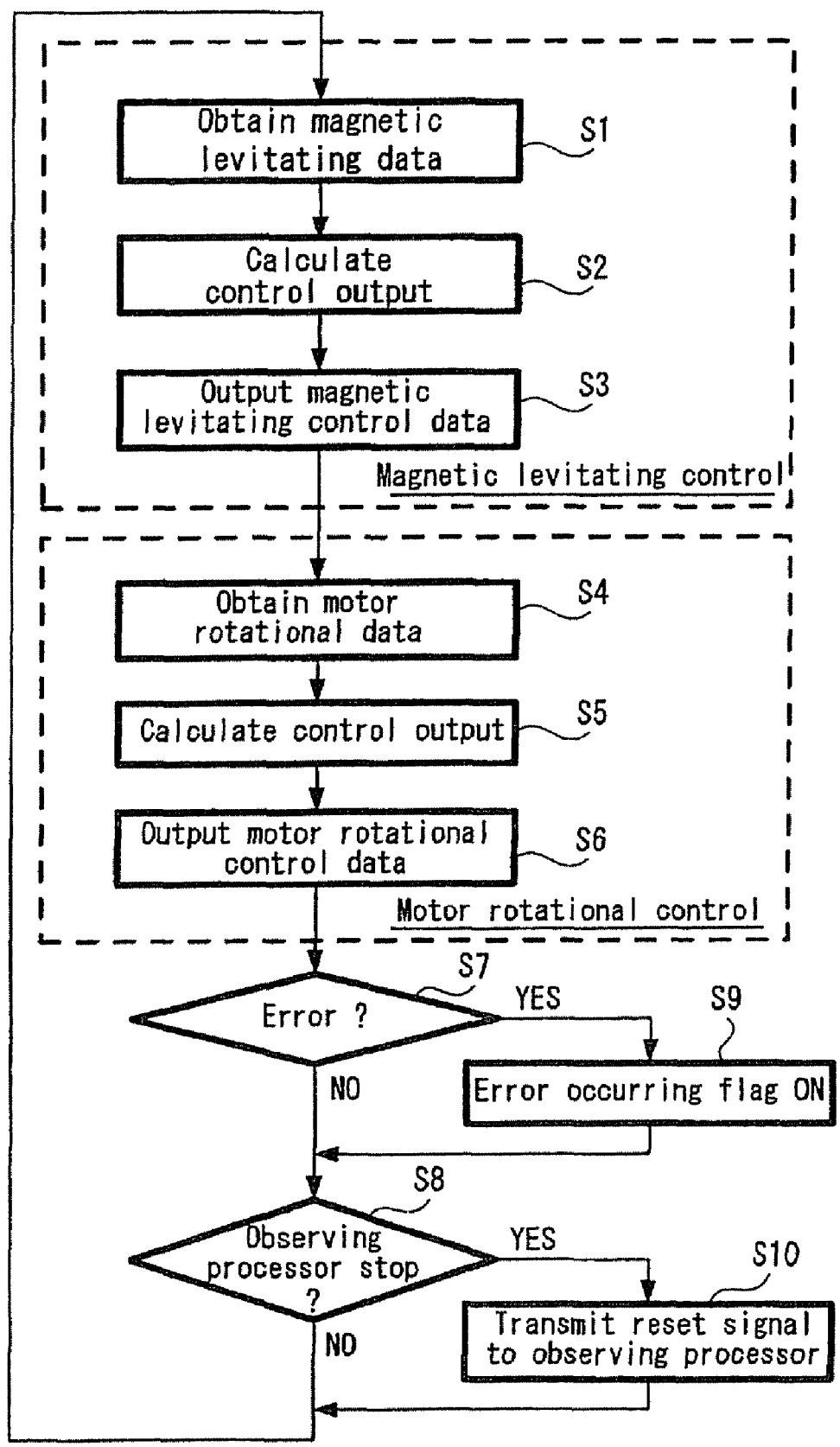
FIG. 5 is a flow diagram to be used for explaining an operation of a controlling processor of an artificial heart pump system according to the present invention.
Figure 6:
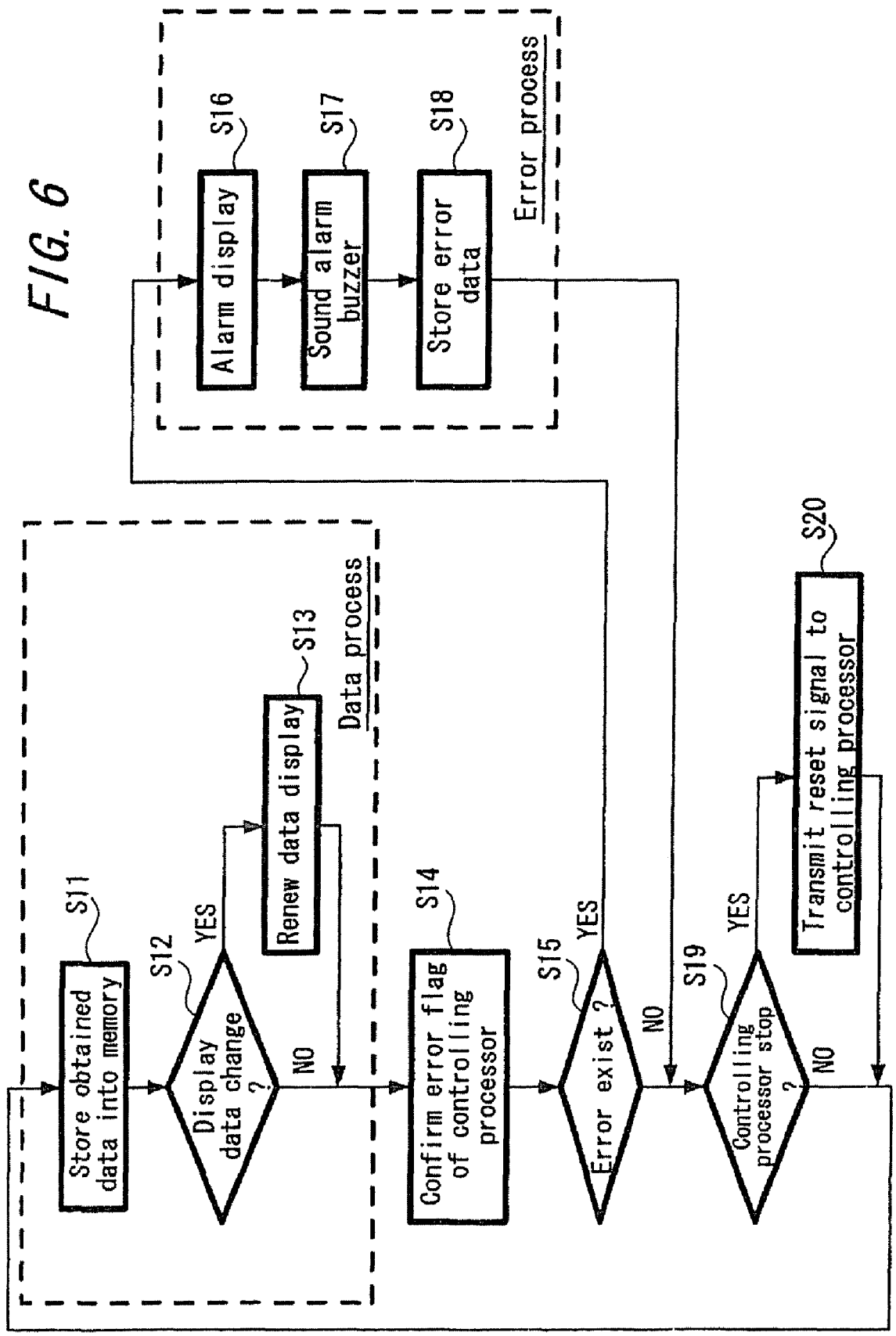
FIG. 6 is a flow diagram to be used for explaining an operation of an observing processor of an artificial heart pump system according to the present invention.

Next, the operation of the artificial heart pump system of the present invention will be explained in more detail according to flow diagrams shown in FIG. 5 and FIG. 6. FIG. 5 is a flow diagram for explaining the operation of the controlling processor 4 in the controller 1 according to the system of the present invention and FIG. 6 is a flow diagram for explaining the operation of the observing processor 5.

First, the operation of the controlling processor 4 will be explained according to the flow diagram of FIG. 5. Firstly, magnetic floating data are obtained from the magnetic floating control circuit 6 by means of the controlling processor 4 (step S1). The controlling processor 4 calculates a control output for controlling a floating status of the impeller in the blood pump 2 according to the obtained data (step S2) and outputs this to the magnetic floating control circuit 6 (step S3). The magnetic floating control of the impeller is completed from the step S1 until the step S3.

Next, in the controlling processor 4, rotational frequency data of the motor are obtained from the motor driving circuit 7 (step S4). The controlling processor 4 calculates control data for controlling the rotational frequency of the motor according to the obtained data (step S5) and supplies this to the motor driving circuit 7 (step S6). The rotational frequency control of the motor is completed from the step S4 until the step S6.

When the magnetic floating control of the impeller and the rotation control of the motor are finished, it is judged subsequently whether or not there is abnormality in the obtained data (step S7). If there is no abnormality in the obtained data (error does not exist), it is judged next whether or not the observing processor 5 is in a stop status (step S8). Then, if the observing processor 5 is in an operation status, the flow returns to step S1 of the first stage shifts to an obtaining cycle of magnetic floating data again, but if the observing processor 5 is in a stop status, a control signal (reset signal) is transmitted from the controlling processor 4 to the observing processor 5 so as to reset the observing processor 5. More specifically, it is made to be in an operation status (step S10). In the judging step S7, in a case when there is abnormality (error exists), an error occurring flag is made ON (step S9), and the flow proceeds to step S8.

Next, the operation of the observing processor 5 will be explained according to a flow diagram of FIG. 6. First, the observing processor 5 stores the obtained data into a memory of the memory device 8 (step S11). Subsequently, it is judged whether or not there is a change in display data displayed on the LED 10 (step S12). If there is a change in the display data, a renewal or update of the data display is performed (step S13) and the flow proceeds to next step. Steps from step S11 to step S13 are data processing steps.

In a case when it is judged in the judging step S12 that there is no change in the display data, the flow proceeds to a next step directly and a confirmation whether or not the error occurring flag of the controlling processor 4 is ON is performed (step S14). Then, it is judged whether or not there was an error as a result of the confirmation of the error occurring flag (step S15).

If it is judged in step S15 that there is an error, the flow is shifted to an error processing flow after step S16. Then, an error display for changing the luminescent color of the LED 11, for example, from green to red color is performed first (step S16) and subsequently, the buzzer 12 is made to sound so as to emanate warning sounds (step S17). Finally, error data are stored into the memory device 8 by means of the observing processor 5 of the controller 1 (step S18).

If it is judged in the judging step S15 that there is no error, it is judged whether or not the controlling processor 4 is in a stop status (step S19). In a case when the controlling processor 4 is in a stop status as a result of this judgment, a reset signal is transmitted from the observing processor 5 with respect to the controlling processor 4 and the controlling processor 4 is made to be a reset status, that is, an operation status (step S20).

If it is judged in the judging step S19 that the controlling processor 4 is not in a stop status, the flow returns again to the data processing step.

According to the exemplified embodiment of the present invention as explained above, the controlling processor 4 for controlling the operation status of the blood pump 2 and the observing processor 5 for performing the saving and displaying the collected data from the blood pump 2 are arranged in the controller 1 and these two processors are made to cooperate each other for communication or the like.

Consequently, the controlling processor 4 can control only the pump independently from the processes of data displaying and saving, so that it becomes possible to maintain the pump function even if the observing processor 5 stops its processor function tentatively.

In addition, by virtue of performing a bilateral observation between the two processors bilaterally and in cooperation, abnormality can be detected and it is possible to carrying out recovery processes trigged by the abnormality detection even in a case when the controlling processor 3 stops its pump control function so longer as the observing processor 5 for displaying and saving the collected data does not stop simultaneously. More specifically, in a case when the processor for observation partner is detected to stop, it becomes possible to make the partner return to the former status speedily by transmitting a reset signal or the like with respect to the partner.

Consequently, the whole artificial heart pump system can be avoided from being stopped and at the same time the load of each processor can be reduced, because it is possible to share the processes by making the observing processor 5 display and save the collected data, by making the controlling processor 4 control the operation status of the blood pump 2 and the like.

Therefore, it becomes possible to improve the operation stability of each of the controlling and observing processors 4 and 5 and also, the total cost of the whole artificial heart pump system can be maintained in a small amount, because relatively low functional devices can be used for respective processors. Further, the software used for each of the controlling and observing processors can be maintained in a small-sized one.

Next, a battery pack for an artificial heart which is used in the artificial heart pump system according to the present invention will be explained.

Figure 3:
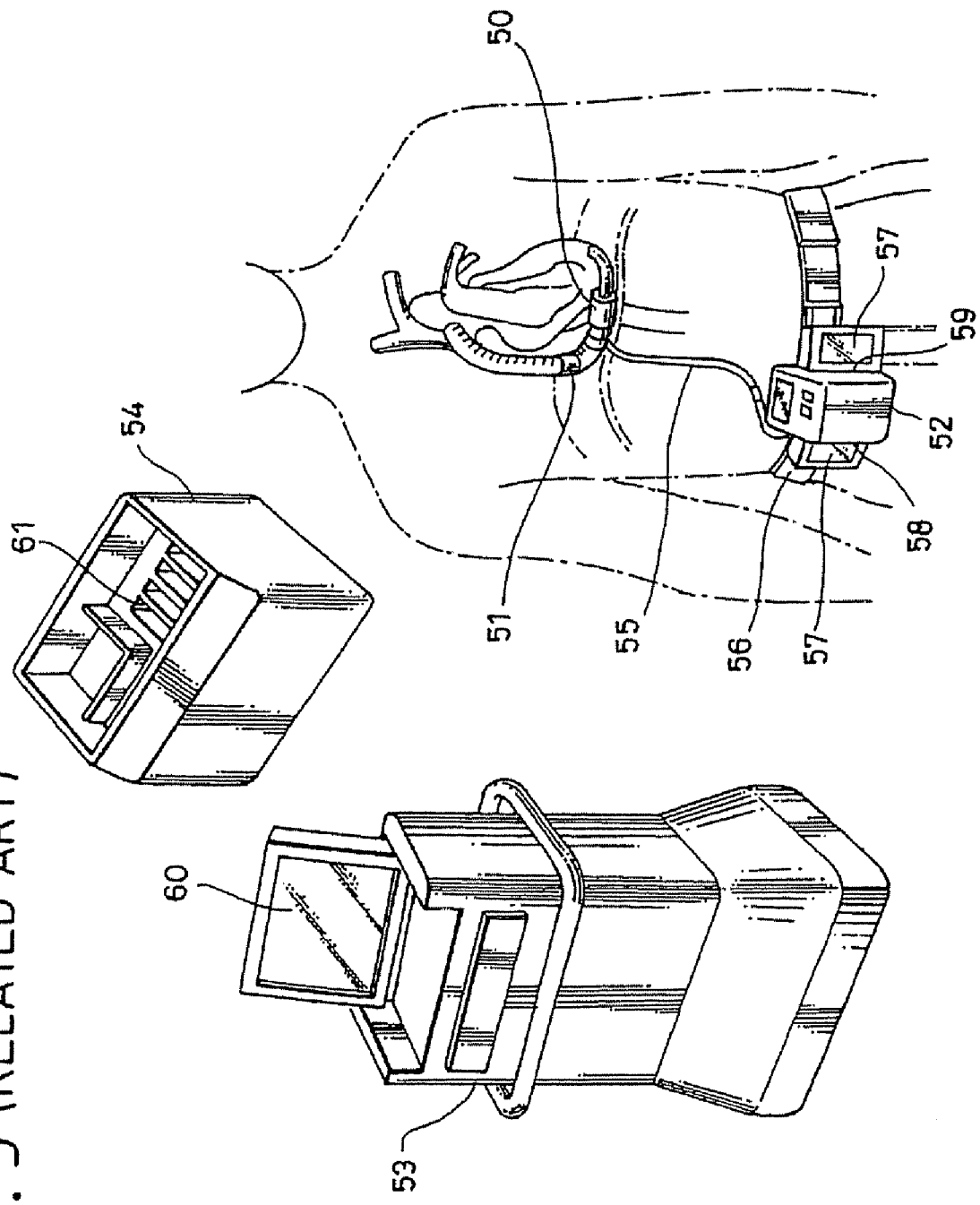
FIG. 3 is a diagram showing an example of a conventional artificial heart pump system attached to and carried by a human body and also showing a battery charger and data collecting apparatus thereof.
Figure 7:
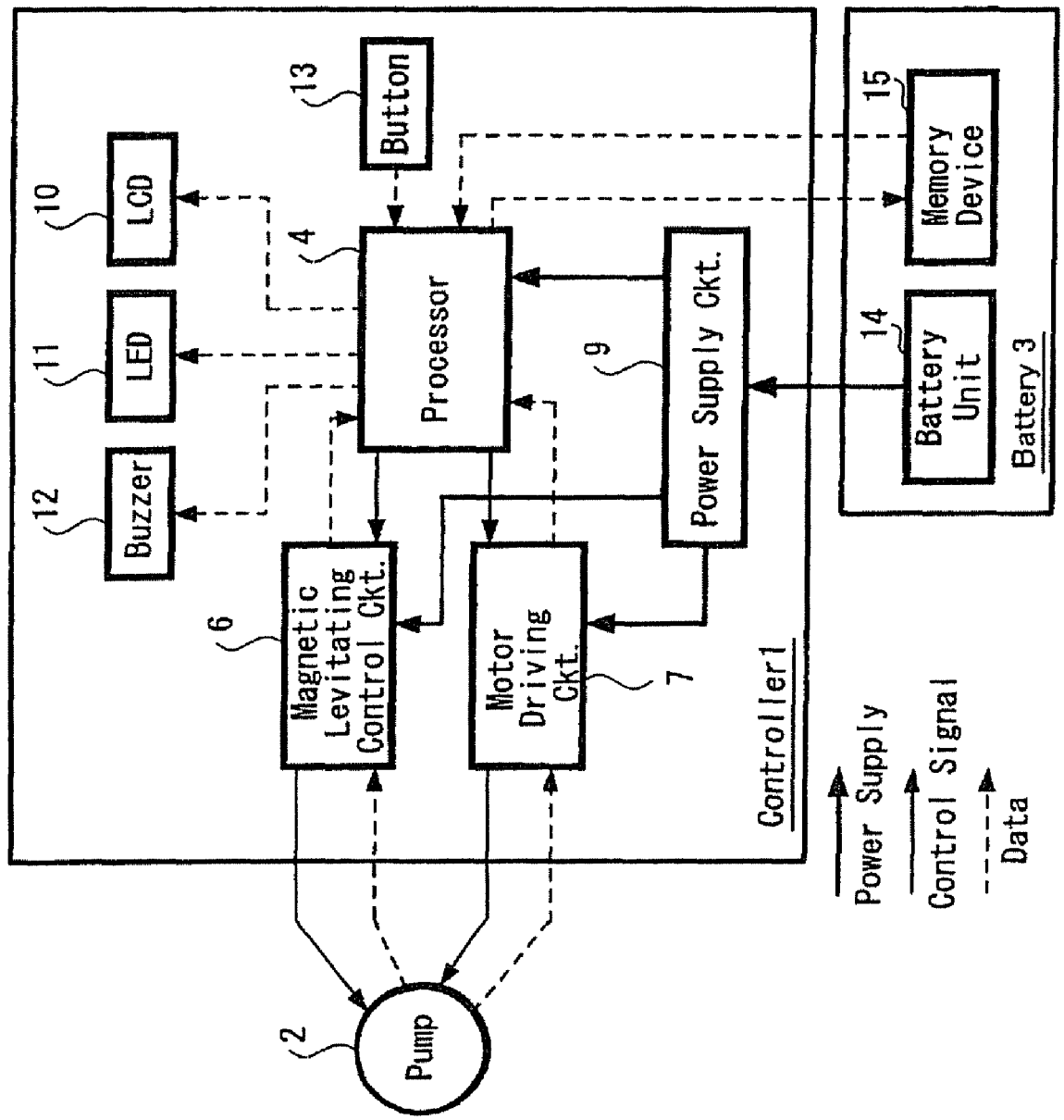
FIG. 7 is a whole constitution block diagram of an artificial heart pump system using a battery pack of a type equipped with a memory device according to the present invention.

FIG. 7 is a block diagram showing a whole constitution of an artificial heart pump system using a battery pack for an artificial heart. The different portion from the conventional artificial heart pump system shown in FIG. 3 lies in that the memory device 104 which was provided in the controller 101 according to the conventional system is provided in a battery pack. Constitutional portions same as the block constitutional diagram shown in FIG. 4 are designated by putting the same reference numerals.

The controller 1 is composed of a controlling processor 4 which supervises the control of a blood pump 2 and a control system in the controller 1; a magnetic floating control circuit 6 for floating an impeller in the blood pump 2 magnetically; a motor driving circuit 7 for driving a motor which rotates the impeller; a power supply circuit 9; a liquid crystal display unit (LCD) 10 for displaying a rotational frequency of the impeller of the blood pump 2, a blood flow rate, a discharging pressure or the like; a light emitting device (LED) 11 for displaying whether or not the operation of the blood pump and the controller is normal; a buzzer 12 for announcing an abnormality of the blood pump and the controller; and an instruction button 13 for instructing, with respect to the processor 4, a change of the pump activation, a change of the LCD displaying content, a release of an abnormal status or the like. The power supply circuit 9 supplies electric power to the processor 4, the magnetic floating control circuit 6 and the motor driving circuit 7. In FIG. 7, the supply of the power supply is designated by the arrow mark of bold solid lines, the flow of the control signals is designated by the arrow mark of thin solid lines and the flow of the data is designated by the arrow mark of dotted lines.

The battery pack 3 for the artificial heart according to the present invention is composed of a battery unit 14 consisting of a charging battery and a memory device 15. With respect to the memory device 15, electric power is supplied from the battery unit 14 and at the same time data showing the operation status of the blood pump 2 is received from the processor 4 of the controller 1 and accumulated therein. Also, data showing the operation condition or the like of the blood pump 2 and accumulated in this memory device 15 are transmitted to the processor 4 such that the control of the magnetic floating control circuit 6 and the motor driving circuit 7 is performed by means of the processor 4.

Next, the operation of the artificial heart pump system shown in FIG. 7 according to the present invention will be explained according to a flow diagram shown in FIG. 8.

Figure 8:
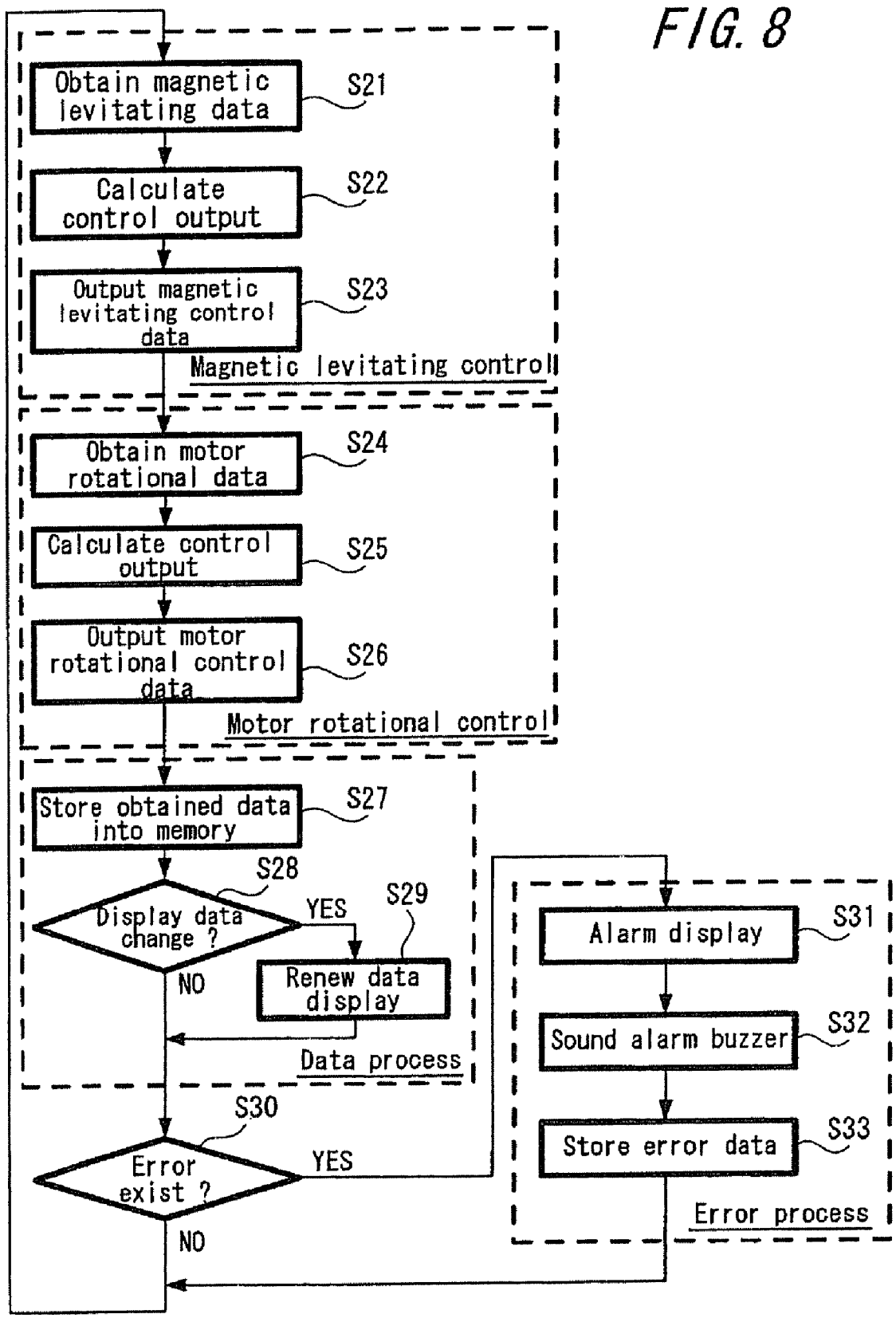
FIG. 8 is a flow diagram to be used for explaining an operation of an artificial heart pump system shown in FIG. 7 according to the present invention.

In the flow diagram of FIG. 8, magnetic floating data are first obtained from the magnetic floating control circuit 6 by means of the processor 4 in the controller 1 (step S21). The processor 4 calculates a control output of a floating status of the impeller in the blood pump 2 according to the obtained data (step S22) and output this to the magnetic floating control circuit 6 (step S23). The magnetic floating control of the impeller is completed by the steps from step S21 to step S23.

Next, in the processor 4, rotation data of the motor is obtained from the motor driving circuit 7 (step S24). The processor 4 calculates rotation control data of the motor according to the obtained data (step S25) and supplies this to the motor driving circuit 7 (step S26). The rotation control of the motor is completed by the steps from the step S24 and the step S26.

When the magnetic floating control of the impeller and the rotation control of the motor is finished, the processor 4 next stores the obtained data into the memory device 15 in the battery pack 3 (step S27). Thereafter, it is judged in the controller 1 whether or not the data displayed on the LED 10 are made changed (step S28). In a case when the display data are necessary to be changed, the change of the display data is instructed to the processor 4 by means of the button 13 of the controller 1, or a keyboard or touch panel which is not shown and data display is made renewed (step S29). The processes from step S27 to step S29 are processes of data processing steps.

Subsequently, it is judged whether or not there is abnormality (step S30). In a case when there is abnormality (error exists), an error display for changing the luminescent color of the LED 11 in the controller 1, for example, from green to red color is performed first (step S31) and at the same time, the buzzer 12 is made to sound (step S32). Then, error data at the abnormal time are stored into the memory device 15 in the battery pack 3 by means of the processor 4 of the controller 1 (step S33). If it is judged in the judging step S30 that there is no error, the flow returns to the first step S21 and acquirement of the magnetic floating data is performed.

Figure 9:
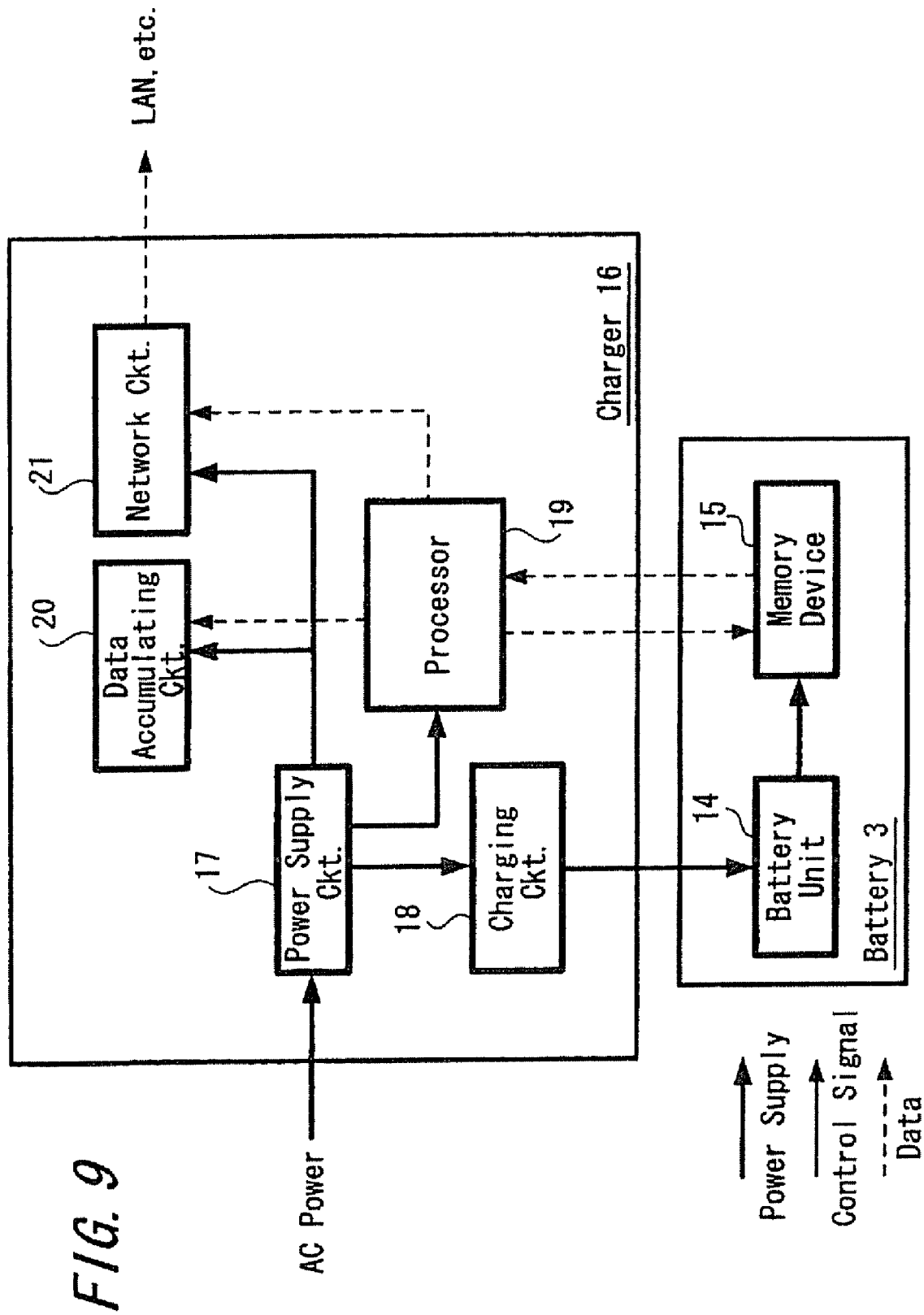
FIG. 9 is a block diagram of a charger having a data collecting function for charging a battery pack to be used in an artificial heart pump system according to the present invention.

FIG. 9 is a block diagram of a charger having a data collecting function for collecting and accumulating data to the memory device 15 of the battery pack 3 shown in FIG. 7.

In FIG. 9, the charger 16 is composed of a power supply circuit 17 supplied with an AC power supply, a charging circuit 18, a processor 19, a data accumulating apparatus 20 controlled by the processor 19 and a network circuit 21. The electric power from the power supply circuit 17 is supplied as shown in bold solid lines to the charging circuit 18, the processor 19, the data accumulating circuit 20 and the network circuit 21.

In the battery charger 16 having data collecting function shown in FIG. 9, charging will start from the charging circuit 18 with respect to the battery unit 14 when the battery pack 3 is coupled with the charger 16 for charging by means of a cable which is not shown and a connector.

Simultaneously, data accumulated in the memory device 15 provided in the battery pack 3 are transmitted to the processor 19 by receiving a reading-out instruction from the processor 19 of the charger 16. The processor 19 memory-saves the data in the data accumulating apparatus 20 of high capacity and at the same time transmits them from the network circuit 21 to a communication line of LAN or the like when it is necessary.

In this manner, data accumulated in the memory device 15 of the battery pack 3 and showing the operation status of the blood pump 2 are saved in the data accumulating apparatus 20 of the charger 16 when charging the battery unit 14 everyday, so that it becomes possible to make the capacity of the memory device 15 compact. In addition, it is possible to transmit these clinical data to a faraway observation unit by means of the communication line of LAN or the like, so that it is also possible to make use of them for early diagnosis.

As mentioned above, in the present invention, the battery pack 3 of the controller 1 for the artificial heart pump which is provided outside the body is equipped with the memory device 15 for data accumulation and data showing the operation status of the blood pump 2, event log or the like is transmitted to the battery pack 3 from the controller 1 by using the communication line and is to be saved in the memory device 15.

Also, it is necessary to perform daily charging to the battery which is used for the artificial heart pump system, so that it is removed from the controller 1 periodically and connected to the battery charger 16. According to the above mentioned example of the exemplified embodiment, data accumulated in the memory device 15 are downloaded to the data accumulating apparatus 20 of high capacity inside the charger 16 by utilizing the charging time for the battery unit 14.

Figure 1:
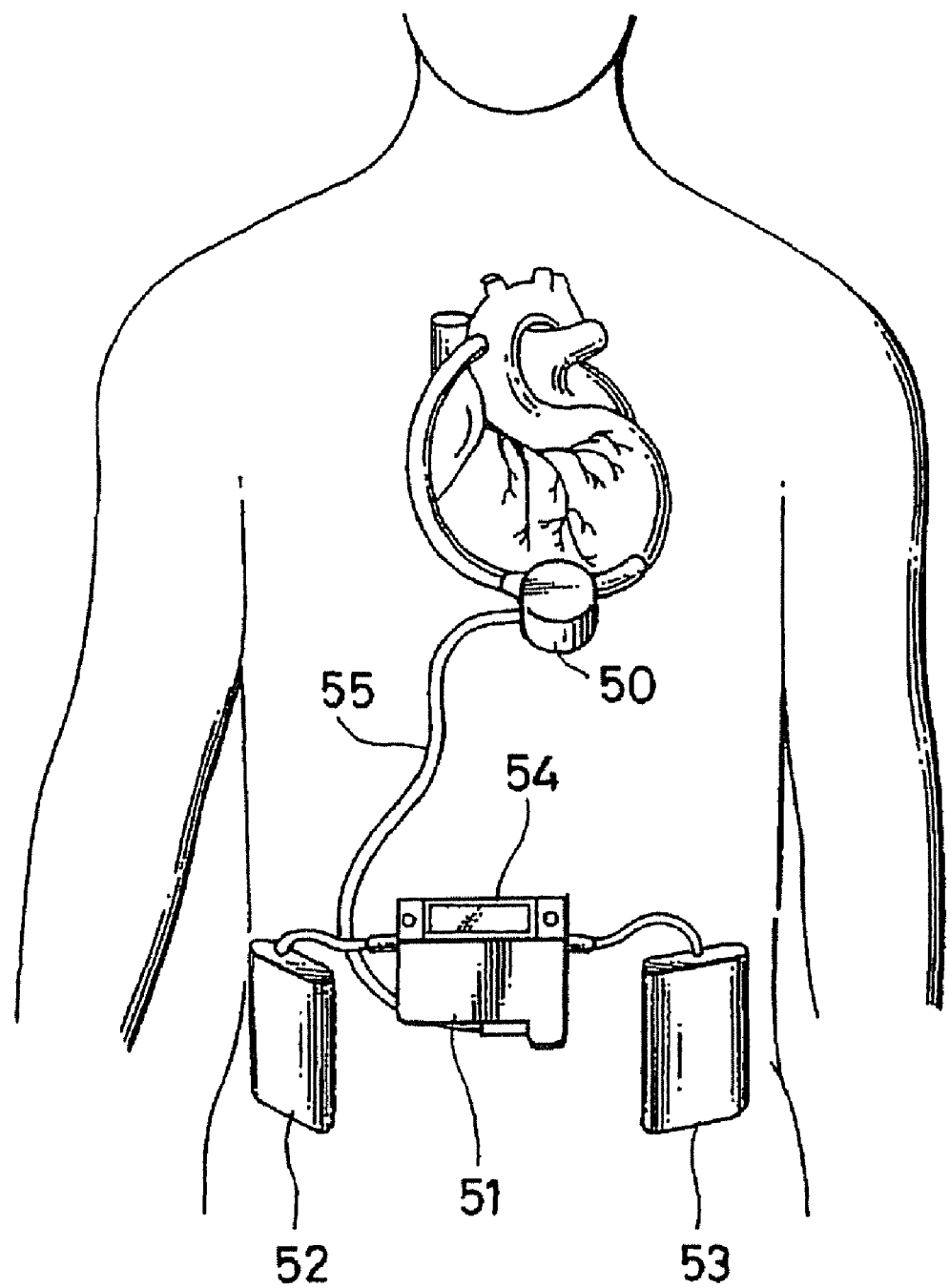
FIG. 1 is a diagram showing an arrangement relation when a conventional artificial heart pump system is attached to and carried by a human body.
Figure 10:
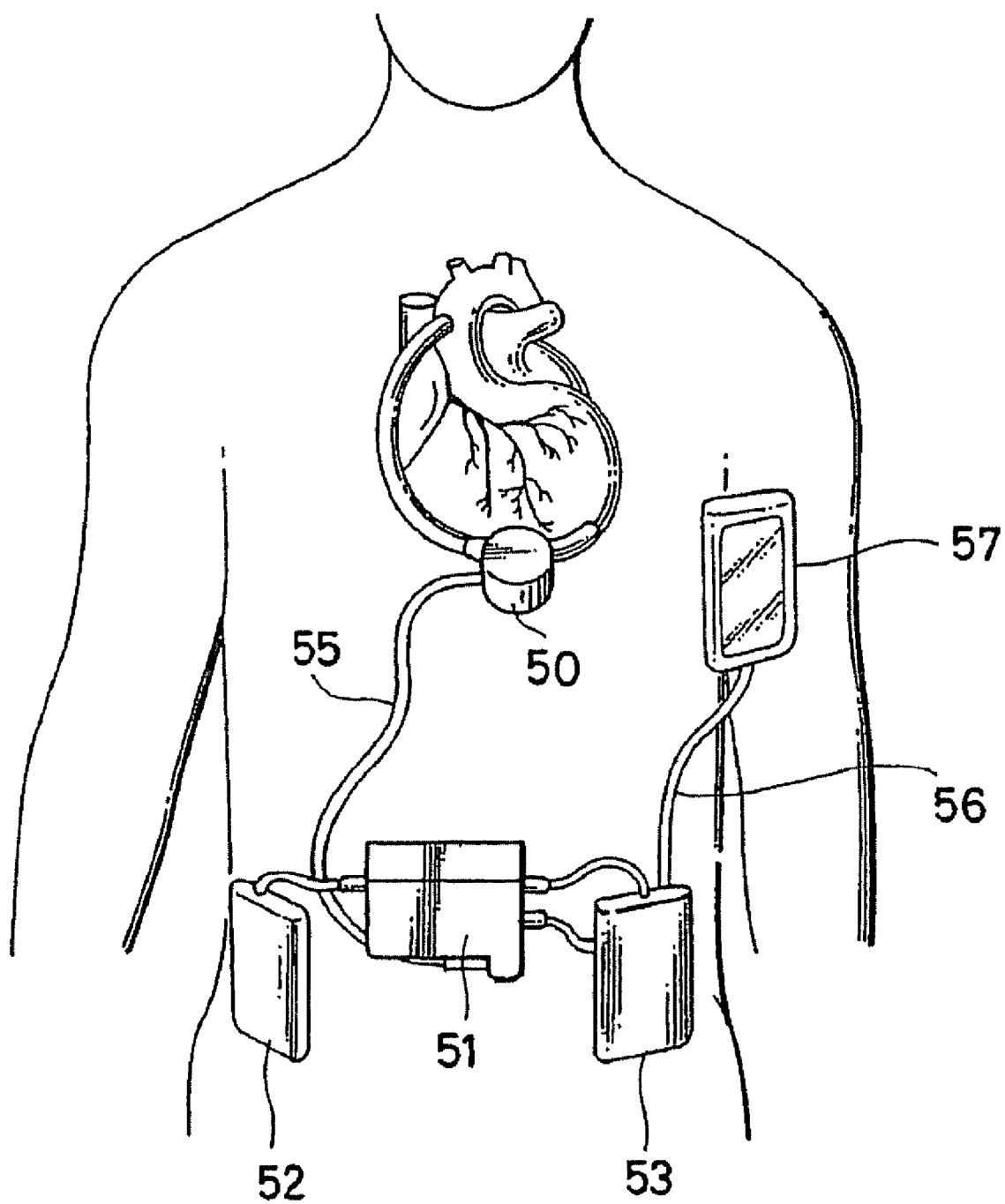
FIG. 10 is a diagram showing an arrangement relation among an artificial heart pump, its controller, battery pack and a user interface unit according to the present invention when they are attached to and carried by a human body.

FIG. 10 shows a whole constitution in a case when the artificial heart pump system according to the present invention is carried on a person. The same constitutions as those of the conventional technology shown in FIG. 1 are designated by putting the same reference numerals therewith. In the arrangement of such an artificial heart pump system, the blood pump 50 implanted inside the human body is connected to the controller 51 which is carried on the outside of the body, for example, such as on a belt portion by means of the cable 55 which passes through the skin. Then, the controller 51 is connected to the batteries 52 and 53 as an electric power supply source and at the same time, it is connected to a user interface unit 57 for displaying the operation status of the blood pump 1 by means of a cable 56.

With respect to the blood pump 50, an inflow entrance of the blood pump 50 is connected to a left ventricle of the heart and the blood is bypassed by connecting the outflow exit to the main artery such that blood stream of a patient whose heart function decreases is to be secured.

The user interface unit 57 is provided with a display unit for performing a display of an operation status of the blood pump 50, that is, a rotational frequency of the impeller, a blood flow rate, discharging pressure and the like in response to a reception of a signal from the controller 2. In addition, it is also provided with an instruction button which is not shown to be used in a case when a setting change or the like of the operation condition is carried out by a user who is a patient or a medical staff with respect to the present system.

Figure 2:
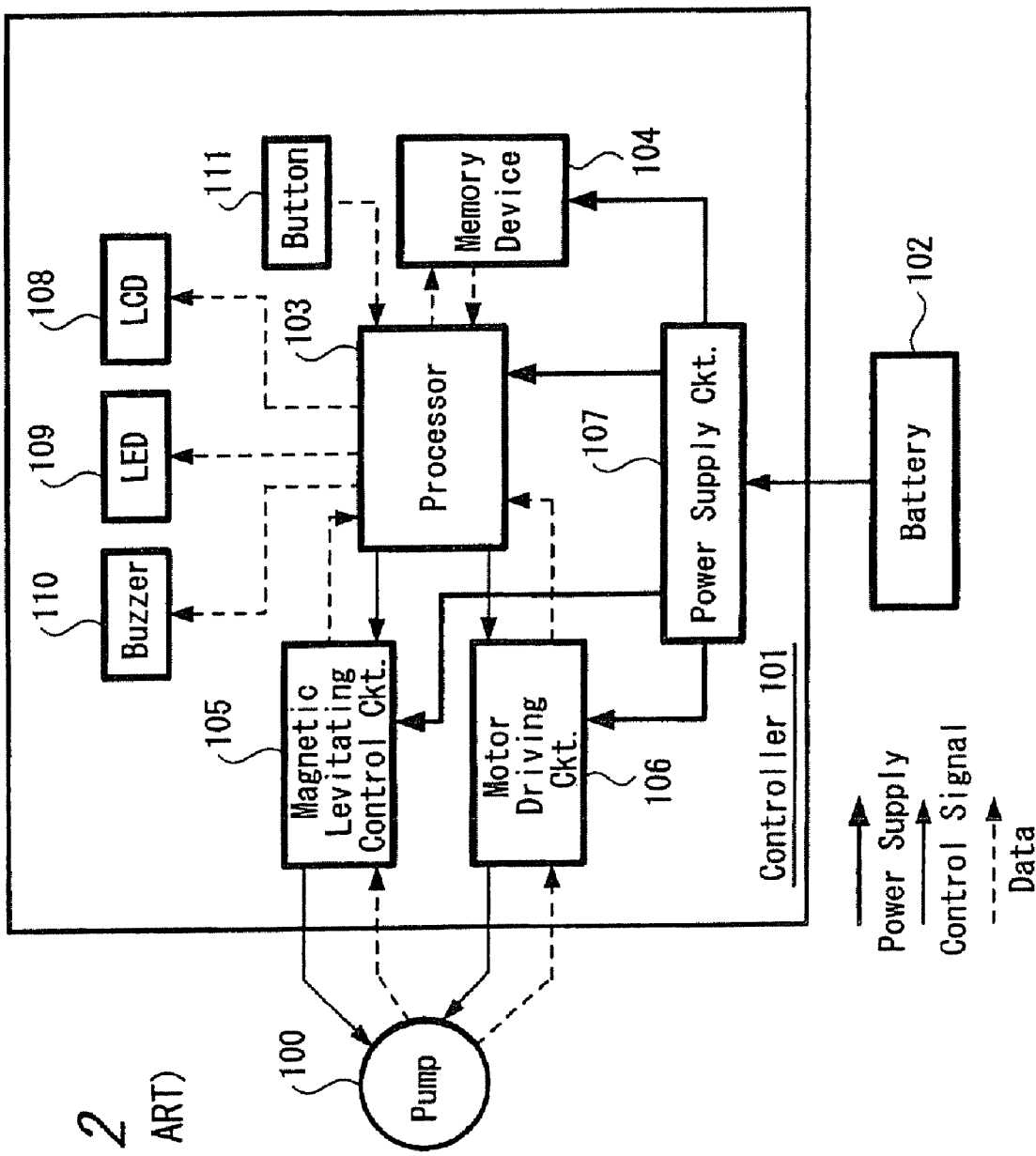
FIG. 2 is a constitutional block diagram showing a conventional artificial heart pump system.
Figure 11:
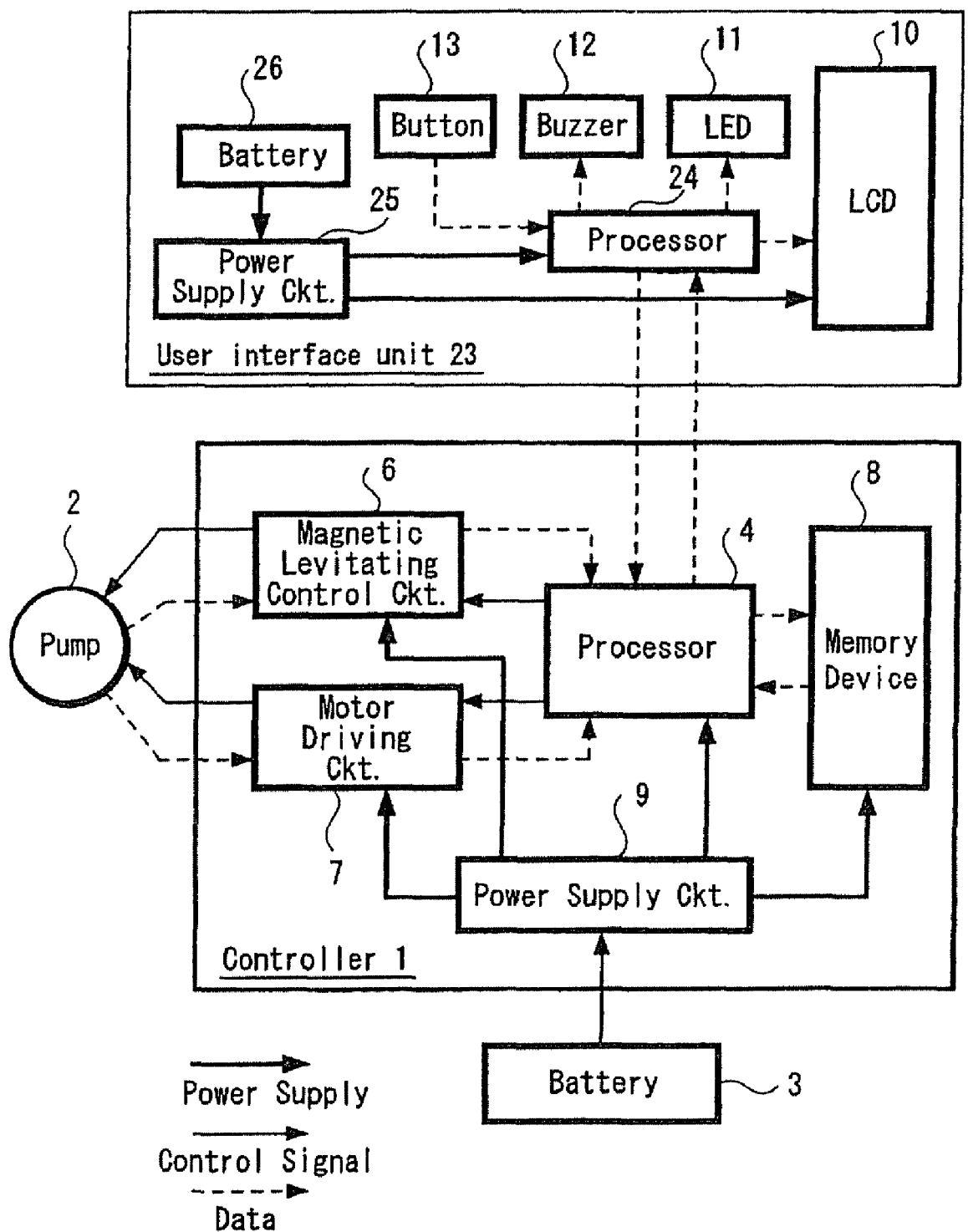
FIG. 11 is a constitutional block diagram showing an exemplified embodiment of an artificial heart pump system according to the present invention where a user interface unit and a control apparatus are separated.

FIG. 11 is a block diagram showing a whole constitution of an artificial heart pump system where a user interface unit is provided separately from a controller according to the present invention. Here, the difference from the conventional artificial heart pump system shown in FIG. 2 lies in a portion where a user interface unit 23 is provide independently from the controller 1. The same reference numerals are put for the same portions as the constitutional elements shown in FIG. 4 and FIG. 7.

This user interface 23 (corresponding to 57 in FIG. 10) is connected to the controller 1 by means of the cable 56 shown in FIG. 10, but it is possible to connect this connection by means of a wireless LAN or the like.

The controller 1 is composed of the processor 4 for supervising the control of the blood pump 2 and the whole controller 1; the memory device 8 for saving an observation result of the operation status of the blood pump, an operation condition of the blood pump and the like; the magnetic floating control circuit 6 for floating the impeller in the blood pump 2 magnetically; the motor driving circuit 7 for driving the motor which rotates the impeller; and the power supply circuit 9.

The power supply circuit 9 is a circuit for supplying electric power to the processor 4, the memory device 8, the magnetic floating control circuit 6, and the motor driving circuit 7.

On the other hand, the user interface unit 23 connected to the controller 1 by means of a cable, a wireless LAN or the like is provided with a processor 24 for a user interface which is connected to the processor 4 of the controller 1; the liquid crystal display unit (LCD) 10 for displaying a rotational frequency of the impeller of the blood pump 2, a blood flow rate, a discharging pressure or the like; the light emitting device (LED) 11 for displaying the operation status of the blood pump and aforesaid controller; the buzzer 12 for announcing an abnormality of the blood pump and aforesaid controller; a power supply circuit 25 for supplying electric power to the processor 24 and LED 10; and a battery 26 as a driving source for the power supply circuit 25. In FIG. 11, the supply of the power supply is designated by the arrow mark of bold solid lines, the flow of the control signals is designated by the arrow mark of thin solid lines and the flow of the data is designated by the arrow mark of dotted lines.

According to the exemplified embodiment of the artificial heart pump of the present invention, it becomes possible to exclude the user interface portion from the controller 1 by making the controller 1 of the artificial heart pump and the user interface unit 23 independent from each other as other modules. In this manner, it becomes unnecessary to access directly to the controller when an operation for confirming a display of the controller or the like is performed or the like and a patient can hide the controller under his clothes or the like. Also, it becomes possible to make the alarm to sound at a portion near the ears by including the buzzer 12 in the user interface unit 23 such that a failure of miss-hearing of the alarm can be avoided.

Also, the controller 1 and the user interface unit 23 can be connected detachably by using a connector, so that it is possible to use it as an easy and/or simple system when the user interface unit 23 is detached when unnecessary. Further, even in a case when the user interface unit 23 is broken down, the system can be made recovered without stopping the system by exchanging only the tip side portion of the connector.

Furthermore, since the user interface portion can be removed from the hardware and software of the controller, it becomes possible to change both of the controller 1 and the user interface unit 23 to ones of easy and/or simple constructions.

Therefore, with respect to the controller 1 used in the artificial heart pump system according to the present invention, it is possible to realize a miniaturization as compared with a conventional one and with respect to the software, it becomes possible to improve the productivity, the maintainability and/or the reliability.

According to the artificial heart pump system of the present invention, even if a trouble occurs in the artificial heart pump system, a controller of an artificial heart pump system is realized with a high reliability where the operation of the pump is maintained or guaranteed as much as possible.

Further, according to the present invention, a plurality of processors are mounted such that even if one processor stops, another processor can continue its operation independently, so that the whole system almost never stops and this effect is large with respect to the safety measures.

In addition, according to the battery charger of the present invention, it is possible to collect and/or manage pump relating data saved in the memory device 13 in the battery pack 11 automatically on the side of the battery charger 14, so that it becomes possible to realize the automatic collection and/or the unitary management of pump data without any needs of specific operations. Further, it becomes necessary to provide a large scale memory device for recording pump data or the like inside the controller 1, so that it becomes possible to contribute to a miniaturization of the controller 1.

Also, according to the present invention, it becomes possible to achieve the automatic collection and/or management of the system data in the assisted artificial heart pump system without adding any special operations. Further, it becomes possible to miniaturize the controller by excluding the memory device from the controller.

Also, according to the artificial heart pump system of the present invention, in a case when the activating circumstance of the blood pump 2 is to be confirmed, the display confirmation, the operation and/or the like can be performed by taking only the user interface unit at hand without exposing the controller 1 outside the clothes. Further, it is possible to reduce the load of the processor 8 of the controller 2, so that it becomes possible to select relatively low-cost processor.

Also, in a case when the user interface unit 23 is broken down, it is not necessary to stop the controller 1 each time thereof, so that it becomes possible to recover the function only by exchanging the user interface unit 23.

By employing the artificial heart pump system and the user interface unit according to the present invention, an artificial heart assist system of a high reliability can be realized where the operation is simple and convenient and at the same time the system is made operated continuously.

Having described preferred embodiments of the invention with reference to the accompanying drawings, it is to be understood that the invention is not limited to those precise embodiments and that various changes and modifications could be effected therein by one skilled in the art without departing from the spirit or scope of the invention as defined in the appended claims.

What is claimed is:

1. An artificial heart pump system comprising:
   a blood pump configured to be implanted inside a body;
   a control apparatus including a processor and configured to be arranged outside of the body in a portable manner for controlling the blood pump, the control apparatus being devoid of a user interface portion of the artificial heart pump system;
   a display unit configured to display an operation status of the blood pump;
   an instruction unit configured to provide the control apparatus with an instruction to alter an operation status of the blood pump;
   an user interface unit configured to include the display unit and the instruction unit; and
   wherein the user interface unit is separate from the control apparatus, is configured to be on the body and is connected to the control apparatus by a wired or a wireless communication line.

2. The artificial heart pump system according to claim 1, wherein the display unit is a liquid crystal display unit for displaying at least one of a rotational speed of an impeller, a blood flow rate, and a discharging pressure of the blood pump.

3. The artificial heart pump system according to claim 1, wherein the user interface unit includes a light emitting device for displaying the operation status of the blood pump and the control apparatus, and a buzzer for notifying an abnormality of the blood pump and the control apparatus.

4. The artificial heart pump system according to claim 1, wherein the user interface unit and the control apparatus independently include a power supply circuit, and the interface unit includes a processor independent from the processor of the control apparatus.

5. The artificial heart pump system according to claim 1, wherein the user interface unit is connected to the control apparatus by a wireless communication line.

6. A user interface unit for use in an artificial heart pump system comprising:
- a first processor configured to be connected to a control apparatus for controlling operation of a blood pump implanted inside a body by a wired or a wireless communication line, the control apparatus including a second processor and being configured to be carried on an outside of the body;
- a liquid crystal display device configured to be controlled by the first processor and display an operation status of the blood pump;
- an alarm device configured to be controlled by the first processor and notify a user about a normal or an abnormal operation status of the blood pump and the control apparatus;
- an instruction device configured to provide the control apparatus through the first processor with an instruction to alter the operation status of the blood pump; and
- wherein the interface unit is configured to be on the body independently from the control apparatus.

7. The user interface unit according to claim 6, wherein the alarm device includes a light emitting device.

8. The user interface unit according to claim 6, wherein the alarm device includes a buzzer.

9. The user interface unit according to claim 6, wherein the interface unit is connected to the control apparatus by a wireless communication line.

10. An artificial heart pump system comprising:
- a blood pump configured to be implanted inside a body;
- a control apparatus configured to be arranged outside of the body in a portable manner and carried on the body, the control apparatus comprising a first processor for controlling the blood pump;
- a user interface unit separate from and movable with respect to the control apparatus so that the user interface unit can be moved to a desired place without also moving the control apparatus, the user interface unit being configured to be on the body; and
- the interface unit which is separate from and movable with respect to the control apparatus comprising:
- a second processor configured to provide the first processor of the control apparatus with instruction to alter an operation status of the blood pump; and
- a display unit configured to display the operation status of the blood pump.

11. The artificial heart pump system according to claim 10, wherein the user interface unit includes an alarm to provide notification about an abnormality of the blood pump.

12. The artificial heart pump system according to claim 10, wherein the user interface unit includes a button configured to be operated by a user to change information displayed on the display unit.

13. The artificial heart pump system according to claim 10, wherein the user interface unit includes a buzzer which provides notification about an abnormality of the blood pump.

14. The artificial heart pump system according to claim 10, wherein the user interface unit includes a light emitting device for displaying the operation status of the blood pump and the control apparatus.

15. The artificial heart pump system according to claim 10, wherein the user interface unit is connected to the control apparatus by a wireless communication line.

* * * * *